United States Patent
Ehrhardt et al.

(10) Patent No.: US 7,320,877 B1
(45) Date of Patent: Jan. 22, 2008

(54) DIHYDROOROTASE EXTRACTED FROM PLANTS

(75) Inventors: Thomas Ehrhardt, Speyer (DE); Jens Lerchl, Ladenburg (DE); Marc Stitt Nigel, Edingen-Neckarhausen (DE); Rita Zrenner, Ladenburg (DE); Michael Schroeder, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 234 days.

(21) Appl. No.: 10/070,277

(22) PCT Filed: Sep. 2, 2000

(86) PCT No.: PCT/EP00/08581

§ 371 (c)(1),
(2), (4) Date: Mar. 6, 2002

(87) PCT Pub. No.: WO01/18190

PCT Pub. Date: Mar. 15, 2001

(30) Foreign Application Priority Data

Sep. 7, 1999 (DE) .............................. 199 42 742

(51) Int. Cl.
*C12Q 1/34* (2006.01)
*C12N 9/14* (2006.01)
*C12N 1/20* (2006.01)
*C12N 15/00* (2006.01)

(52) U.S. Cl. .................... 435/18; 435/195; 435/252.3; 435/320.1; 536/23.2; 530/350

(58) Field of Classification Search ................ 435/18, 435/195, 252.3, 320.1; 536/23.2; 530/350
See application file for complete search history.

(56) References Cited

FOREIGN PATENT DOCUMENTS

WO 01/14569 3/2001

OTHER PUBLICATIONS

Sequence alignment between Applicants' SEQ ID No. 2 and Accession No. T05124.*
Sequence alignment between Applicants' SEQ ID No. 1 and Accession No. Accession AF000146.*
Bowie et al., 1990. Science, vol. 247, pp. 1306 1310, especially p. 1306, col. 2, paragraph 2.*
Mol.Gen.Genet,207(2-3),314-319(1987)Souciet et al. XP-002165268—AF000146.
Christopherson et al., XP-000997720,Bio.Soc.Trans.
Christopherson etal.,XP-002165266,Biochem.1989,463-470.
Dihydroorotate Dehydrogenase, Miller,63-69.
Analytical Biochem.32,408-419(1969) Prescott et al.
Plant Jrl.,417-422(1992),Minet et al.
Plant Physiol., PGR97-114, 1569.
Acta Biochimica Polonica,vol. 15, 1968,No. 4,Mazus et al.
Plant Physiol.(1995)107:469-477, Hoefgen et al. XP-002165269-AI895210.

* cited by examiner

*Primary Examiner*—Tekchand Saidha
(74) *Attorney, Agent, or Firm*—Novak Druce & Quigg, LLP

(57) ABSTRACT

The present invention relates to a DNA encoding a polypeptide with dihydroorotase (EC 3.5.2.3) activity. Also, the invention relates to the use of this nucleic acid for the generation of an assay system.

17 Claims, 2 Drawing Sheets

Figure 2:

Dihydroorotase protein quantity in leaf and tuber of selected transformants of line ROSa leaf                          tuber
WT   40   19   9   3    WT   19   9   3

Dihydroorotase mRNA contents in fully grown leaves of selected transformants of line ROSa 3    9    10   31   34   WT 1.6 kb sense
1.1 kb antisense

SEQUENCE LISTING

<160> NUMBER OF SEQ ID NOS: 9

<210> SEQ ID NO 1
<211> LENGTH: 1271
<212> TYPE: DNA
<213> ORGANISM: Solanum tuberosum
<220> FEATURE:
<221> NAME/KEY: CDS
<222> LOCATION: (9)..(1046)

<400> SEQUENCE: 1

```
ttgcaaaa atg gag ctc tca atc aca caa cct gat gat tgg cat ctt cat      50
         Met Glu Leu Ser Ile Thr Gln Pro Asp Asp Trp His Leu His
         1               5                   10 ctc cgt gat ggt gat gtt ctt aag gca gtt gtc tct cac agt gca cat       98
Leu Arg Asp Gly Asp Val Leu Lys Ala Val Val Ser His Ser Ala His
15                  20                  25                  30 cac ttt ggg agg gca ata gtc atg cca aat ttg aag cct cct atc act      146
His Phe Gly Arg Ala Ile Val Met Pro Asn Leu Lys Pro Pro Ile Thr
                35                  40                  45 acc act gct gct gct gta gca tac cgg gag gcg ata ttg aaa tct tta      194
Thr Thr Ala Ala Ala Val Ala Tyr Arg Glu Ala Ile Leu Lys Ser Leu
            50                  55                  60 cct gtt gat agt gat ttc aac cct ctt atg aca ctt tat ttg aca gat      242
Pro Val Asp Ser Asp Phe Asn Pro Leu Met Thr Leu Tyr Leu Thr Asp
65                  70                  75 aca acc agt cct atg gaa atc aaa cta gca aga gag agc cag gtc gta      290
Thr Thr Ser Pro Met Glu Ile Lys Leu Ala Arg Glu Ser Gln Val Val
        80                  85                  90 ttt ggg gtg aag ttg tac cct gct ggt gcc acg aca aat tct caa gat      338
Phe Gly Val Lys Leu Tyr Pro Ala Gly Ala Thr Thr Asn Ser Gln Asp
95                  100                 105                 110 gga gtg act gat ctt ttc ggg aag tgt tta cca gtt cta caa gaa atg      386
Gly Val Thr Asp Leu Phe Gly Lys Cys Leu Pro Val Leu Gln Glu Met
                115                 120                 125 gtt gag cat aat atg cct ctg ctg gtt cat gga gag gtt act aat cct      434
Val Glu His Asn Met Pro Leu Leu Val His Gly Glu Val Thr Asn Pro
            130                 135                 140 gag gtt gac atg ttt gat aga gaa aag gta ttc att gaa acg gtt cta      482
Glu Val Asp Met Phe Asp Arg Glu Lys Val Phe Ile Glu Thr Val Leu
145                 150                 155 aga ccg ttg gtg cag aaa ttt cca caa ttg aag gtc gtg atg gag cat      530
Arg Pro Leu Val Gln Lys Phe Pro Gln Leu Lys Val Val Met Glu His
        160                 165                 170 gtt acc acc att gat gct gtt aag ttt gtt gaa tct tgc act gaa gga      578
Val Thr Thr Ile Asp Ala Val Lys Phe Val Glu Ser Cys Thr Glu Gly
175                 180                 185                 190 ttt gtt gca gca act gtc acc cca caa cat ctt gtt ttg aac agg aat      626
Phe Val Ala Ala Thr Val Thr Pro Gln His Leu Val Leu Asn Arg Asn
                195                 200                 205 tct ctc ttc caa ggg ggc tta caa ccg cat aat tac tgc ctt cca gtc      674
Ser Leu Phe Gln Gly Gly Leu Gln Pro His Asn Tyr Cys Leu Pro Val
            210                 215                 220 ctc aaa aga gag atc cac agg gag gca ctt gtg tca gct gta aca agt      722
Leu Lys Arg Glu Ile His Arg Glu Ala Leu Val Ser Ala Val Thr Ser
```

```
                  225                 230                 235
gga agt aaa aga ttt ttt ctt ggg act gat agt gct cct cat gat aga       770
Gly Ser Lys Arg Phe Phe Leu Gly Thr Asp Ser Ala Pro His Asp Arg
    240                 245                 250 cga aga aaa gag tgt tct tgt gga tgt gct ggt att tac aat gca cct       818
Arg Arg Lys Glu Cys Ser Cys Gly Cys Ala Gly Ile Tyr Asn Ala Pro
255                 260                 265                 270 gta gcc ttg tca gta tat gcg aag gtg ttt gaa aag gaa aat gca ctc       866
Val Ala Leu Ser Val Tyr Ala Lys Val Phe Glu Lys Glu Asn Ala Leu
                275                 280                 285 gac aag ctt gaa gca ttc act agc ttc aat gga cca gat ttt tat ggg       914
Asp Lys Leu Glu Ala Phe Thr Ser Phe Asn Gly Pro Asp Phe Tyr Gly
        290                 295                 300 ctt cct agg aac aac tca aag att aag ttg agt aag acg cca tgg aag       962
Leu Pro Arg Asn Asn Ser Lys Ile Lys Leu Ser Lys Thr Pro Trp Lys
            305                 310                 315 gta ccc gaa tcc ttt tct tat gca tca gga gat att att ccc atg ttt      1010
Val Pro Glu Ser Phe Ser Tyr Ala Ser Gly Asp Ile Ile Pro Met Phe
    320                 325                 330 gct ggt gaa atg ctc gac tgg ttg ccg gct cct ctc tgagaatcat           1056
Ala Gly Glu Met Leu Asp Trp Leu Pro Ala Pro Leu
335                 340                 345 ttgtcattct tgtactgtaa tattgtgatt caaccaaaga tatagactgt aggtgtatca    1116
tcttttcttt catgttgatt agatattatc acgatgataa tatcctttca gctaataaat    1176
tatggaaaca ataagctttg cacgctcacc aaagtgctcc tgtattctga agttcttaaa    1236
ttgttcgttt gattttgaag atttactgat aaaaa                               1271

<210> SEQ ID NO 2
<211> LENGTH: 346
<212> TYPE: PRT
<213> ORGANISM: Solanum tuberosum

<400> SEQUENCE: 2

Met Glu Leu Ser Ile Thr Gln Pro Asp Asp Trp His Leu His Leu Arg
  1               5                  10                  15

Asp Gly Asp Val Leu Lys Ala Val Val Ser His Ser Ala His His Phe
             20                  25                  30

Gly Arg Ala Ile Val Met Pro Asn Leu Lys Pro Pro Ile Thr Thr Thr
         35                  40                  45

Ala Ala Ala Val Ala Tyr Arg Glu Ala Ile Leu Lys Ser Leu Pro Val
     50                  55                  60

Asp Ser Asp Phe Asn Pro Leu Met Thr Leu Tyr Leu Thr Asp Thr Thr
 65                  70                  75                  80

Ser Pro Met Glu Ile Lys Leu Ala Arg Glu Ser Gln Val Val Phe Gly
                 85                  90                  95

Val Lys Leu Tyr Pro Ala Gly Ala Thr Thr Asn Ser Gln Asp Gly Val
            100                 105                 110

Thr Asp Leu Phe Gly Lys Cys Leu Pro Val Leu Gln Glu Met Val Glu
        115                 120                 125

His Asn Met Pro Leu Leu Val His Gly Glu Val Thr Asn Pro Glu Val
    130                 135                 140

Asp Met Phe Asp Arg Glu Lys Val Phe Ile Glu Thr Val Leu Arg Pro
145                 150                 155                 160

Leu Val Gln Lys Phe Pro Gln Leu Lys Val Val Met Glu His Val Thr
                165                 170                 175
```

```
Thr Ile Asp Ala Val Lys Phe Val Glu Ser Cys Thr Glu Gly Phe Val
            180                 185                 190

Ala Ala Thr Val Thr Pro Gln His Leu Val Leu Asn Arg Asn Ser Leu
        195                 200                 205

Phe Gln Gly Gly Leu Gln Pro His Asn Tyr Cys Leu Pro Val Leu Lys
    210                 215                 220

Arg Glu Ile His Arg Glu Ala Leu Val Ser Ala Val Thr Ser Gly Ser
225                 230                 235                 240

Lys Arg Phe Phe Leu Gly Thr Asp Ser Ala Pro His Asp Arg Arg Arg
                245                 250                 255

Lys Glu Cys Ser Cys Gly Cys Ala Gly Ile Tyr Asn Ala Pro Val Ala
            260                 265                 270

Leu Ser Val Tyr Ala Lys Val Phe Glu Lys Glu Asn Ala Leu Asp Lys
        275                 280                 285

Leu Glu Ala Phe Thr Ser Phe Asn Gly Pro Asp Phe Tyr Gly Leu Pro
    290                 295                 300

Arg Asn Asn Ser Lys Ile Lys Leu Ser Lys Thr Pro Trp Lys Val Pro
305                 310                 315                 320

Glu Ser Phe Ser Tyr Ala Ser Gly Asp Ile Ile Pro Met Phe Ala Gly
                325                 330                 335

Glu Met Leu Asp Trp Leu Pro Ala Pro Leu
            340                 345
```

<210> SEQ ID NO 3
<211> LENGTH: 1962
<212> TYPE: DNA
<213> ORGANISM: Nicotiana tabacum
<220> FEATURE:
<221> NAME/KEY: CDS
<222> LOCATION: (305)..(1678)

<400> SEQUENCE: 3

```
gaattcggca cgagcacaaa agtagaaagg gttttgctct ccccttttcat ctgtgtctca      60 taactgtgct aaaacctctc ccatcttccc tcaagaacaa agccaccca aaacaccacc      120 ttgtacactc ccattgtcgc ttccagtttt gtgccccaaa taacctttc agtcatttgt      180 atcttagcat caacaacagt tgctgtctct cttttgttcg tccaatatac tgagcatttt      240
ttgagtagta atttgaaggg tttattcagt tgttaaatat ttgattttttg ttttgtttaa     300 gaaa atg aga caa agg gtt gga ttt gca ttg att aga gaa agc ttg tat      349
     Met Arg Gln Arg Val Gly Phe Ala Leu Ile Arg Glu Ser Leu Tyr
       1               5                  10                  15 cgt aag cta aaa cca agc tct gtt ccc aga cat tat tgc act tct tct      397
Arg Lys Leu Lys Pro Ser Ser Val Pro Arg His Tyr Cys Thr Ser Ser
             20                  25                  30 tca gct aat gtt cct cct att cct cca cct aag att cct cat tct tct      445
Ser Ala Asn Val Pro Pro Ile Pro Pro Pro Lys Ile Pro His Ser Ser
         35                  40                  45 aaa aag gga agg ttg ttt aca gga gcc act att ggt cta cta ata gct      493
Lys Lys Gly Arg Leu Phe Thr Gly Ala Thr Ile Gly Leu Leu Ile Ala
     50                  55                  60 ggg gga gct tat gca agt acg gtt gat gag gcc acc ttc tgt ggc tgg      541
Gly Gly Ala Tyr Ala Ser Thr Val Asp Glu Ala Thr Phe Cys Gly Trp
 65                  70                  75 cta ttc tca gca aca aaa cta gta aat ccg ttc ttt gca ttt ctg gat      589
Leu Phe Ser Ala Thr Lys Leu Val Asn Pro Phe Phe Ala Phe Leu Asp
             80                  85                  90                  95 cca gag gtt gct cac aaa ctg gcg gtc tct gct gca gcc cga gga tgg      637
```

|  |  |
|---|---|
| Pro Glu Val Ala His Lys Leu Ala Val Ser Ala Ala Arg Gly Trp<br>               100                     105               110 |  |
| gtt cca agg gag aag agg cca gat cct cct ata ttg ggc ctt gat gtg<br>Val Pro Arg Glu Lys Arg Pro Asp Pro Pro Ile Leu Gly Leu Asp Val<br>             115                     120               125 | 685 |
| tgg gga aga agg ttc tca aat cct gtt ggt ctt gct gct ggt ttt gac<br>Trp Gly Arg Arg Phe Ser Asn Pro Val Gly Leu Ala Ala Gly Phe Asp<br>        130                     135               140 | 733 |
| aag aat gct gag gct gtt gaa gga ttg ctt gga tta ggt ttt ggc ttt<br>Lys Asn Ala Glu Ala Val Glu Gly Leu Leu Gly Leu Gly Phe Gly Phe<br>145                   150                   155 | 781 |
| gtt gag gtt ggc tca gta act ccc att cca cag gaa ggc aac cca aaa<br>Val Glu Val Gly Ser Val Thr Pro Ile Pro Gln Glu Gly Asn Pro Lys<br>160                   165                   170             175 | 829 |
| cca cgt ata ttt agg ttg cca aat gaa ggt gct ata ata aat agg tgt<br>Pro Arg Ile Phe Arg Leu Pro Asn Glu Gly Ala Ile Ile Asn Arg Cys<br>             180                     185               190 | 877 |
| ggc ttc aat agt gaa gga atc gtt gtg gtt gcc aaa cga ttg ggt gct<br>Gly Phe Asn Ser Glu Gly Ile Val Val Val Ala Lys Arg Leu Gly Ala<br>                195                   200               205 | 925 |
| cag cat ggt aag aga aag ttg gaa aca tct agt act tca tct cca gct<br>Gln His Gly Lys Arg Lys Leu Glu Thr Ser Ser Thr Ser Ser Pro Ala<br>        210                     215               220 | 973 |
| gga gat gaa gtc aag cat gga ggg aaa gct ggt cct ggt att ctt ggt<br>Gly Asp Glu Val Lys His Gly Gly Lys Ala Gly Pro Gly Ile Leu Gly<br>225                   230                   235 | 1021 |
| gtt aac ctt gga aag aat aaa aca agt gaa gac gct gca gca gat tat<br>Val Asn Leu Gly Lys Asn Lys Thr Ser Glu Asp Ala Ala Ala Asp Tyr<br>240                   245                   250             255 | 1069 |
| gtg caa gga gtc cat aca tta tct cag tat gct gac tac ttg gta att<br>Val Gln Gly Val His Thr Leu Ser Gln Tyr Ala Asp Tyr Leu Val Ile<br>                    260                   265              270 | 1117 |
| aat atc tca tcc cca aat act cca gga cta cgc cag ctt cag gga aga<br>Asn Ile Ser Ser Pro Asn Thr Pro Gly Leu Arg Gln Leu Gln Gly Arg<br>             275                     280               285 | 1165 |
| aag cag ttg aag gat ctt gtg aag aag gtt caa gca gct cgt gat gaa<br>Lys Gln Leu Lys Asp Leu Val Lys Lys Val Gln Ala Ala Arg Asp Glu<br>        290                     295               300 | 1213 |
| atg cag tgg ggt gag gaa gga cct ccg cct tta ctt gtg aaa att gct<br>Met Gln Trp Gly Glu Glu Gly Pro Pro Pro Leu Leu Val Lys Ile Ala<br>305                   310                   315 | 1261 |
| cca gat ttg tct aaa caa gat ctt gaa gat att gca gtg gtg gct gtt<br>Pro Asp Leu Ser Lys Gln Asp Leu Glu Asp Ile Ala Val Val Ala Val<br>320                   325                   330             335 | 1309 |
| gct ctt cgt gtg gat gga ctg att ata tca aat act act gtc caa aga<br>Ala Leu Arg Val Asp Gly Leu Ile Ile Ser Asn Thr Thr Val Gln Arg<br>                    340                   345              350 | 1357 |
| cca gat tcc ata agt caa aac cct gtg gct caa gag gct ggt ggc ttg<br>Pro Asp Ser Ile Ser Gln Asn Pro Val Ala Gln Glu Ala Gly Gly Leu<br>             355                     360               365 | 1405 |
| agt ggg aag cca ctc ttt gac atg tca aca aat ata ctg aag gag atg<br>Ser Gly Lys Pro Leu Phe Asp Met Ser Thr Asn Ile Leu Lys Glu Met<br>        370                     375               380 | 1453 |
| tac gtt ctg act aag gga agg att cct ctg att ggc act ggg ggt att<br>Tyr Val Leu Thr Lys Gly Arg Ile Pro Leu Ile Gly Thr Gly Gly Ile<br>385                   390                   395 | 1501 |
| agc agt ggc gag gat gct tac aag aaa att cga gct ggt gcc act ctt<br>Ser Ser Gly Glu Asp Ala Tyr Lys Lys Ile Arg Ala Gly Ala Thr Leu<br>400                   405                   410             415 | 1549 |

```
gtt cag ctt tat aca gca ttt gca tat gga ggc cct gca ctt atc ccc    1597
Val Gln Leu Tyr Thr Ala Phe Ala Tyr Gly Gly Pro Ala Leu Ile Pro
            420                 425                 430 gat ata aag gat gaa ctt gct cgt tgc tta gaa aag gat ggt tat aag    1645
Asp Ile Lys Asp Glu Leu Ala Arg Cys Leu Glu Lys Asp Gly Tyr Lys
            435                 440                 445 tca atc agt gag gct gtt gga gca gac tgc aga tagtagtagt tgatatacta  1698
Ser Ile Ser Glu Ala Val Gly Ala Asp Cys Arg
            450                 455 aaccagtctt ttgagtttga ggggcagagc acatttttgc cacttataat aaatgatata  1758
tttatggttt cctcccatgt ggcgtcatat catttgcttc gtaatttgtg atgtcttccc  1818
aaattttagc tgtttaggga ttactcgtgg caggtgaccc gtattttga aatgtaatat   1878 aggaacgaaa ctttgtatgt ttggttgagt tttttcttga tatggaatta aatccacaca  1938
aaaaaaaaaa aaaaaaaga attc                                          1962

<210> SEQ ID NO 4
<211> LENGTH: 458
<212> TYPE: PRT
<213> ORGANISM: Nicotiana tabacum

<400> SEQUENCE: 4

Met Arg Gln Arg Val Gly Phe Ala Leu Ile Arg Glu Ser Leu Tyr Arg
1               5                   10                  15

Lys Leu Lys Pro Ser Ser Val Pro Arg His Tyr Cys Thr Ser Ser Ser
            20                  25                  30

Ala Asn Val Pro Pro Ile Pro Pro Lys Ile Pro His Ser Ser Lys
        35                  40                  45

Lys Gly Arg Leu Phe Thr Gly Ala Thr Ile Gly Leu Leu Ile Ala Gly
    50                  55                  60

Gly Ala Tyr Ala Ser Thr Val Asp Glu Ala Thr Phe Cys Gly Trp Leu
65                  70                  75                  80

Phe Ser Ala Thr Lys Leu Val Asn Pro Phe Ala Phe Leu Asp Pro
                85                  90                  95

Glu Val Ala His Lys Leu Ala Val Ser Ala Ala Arg Gly Trp Val
                100                 105                 110

Pro Arg Glu Lys Arg Pro Asp Pro Ile Leu Gly Leu Asp Val Trp
            115                 120                 125

Gly Arg Arg Phe Ser Asn Pro Val Gly Leu Ala Ala Gly Phe Asp Lys
130                 135                 140

Asn Ala Glu Ala Val Glu Gly Leu Leu Gly Leu Gly Phe Gly Phe Val
145                 150                 155                 160

Glu Val Gly Ser Val Thr Pro Ile Pro Gln Glu Gly Asn Pro Lys Pro
                165                 170                 175

Arg Ile Phe Arg Leu Pro Asn Glu Gly Ala Ile Ile Asn Arg Cys Gly
            180                 185                 190

Phe Asn Ser Glu Gly Ile Val Val Ala Lys Arg Leu Gly Ala Gln
        195                 200                 205

His Gly Lys Arg Lys Leu Glu Thr Ser Ser Thr Ser Ser Pro Ala Gly
    210                 215                 220

Asp Glu Val Lys His Gly Gly Lys Ala Gly Pro Gly Ile Leu Gly Val
225                 230                 235                 240

Asn Leu Gly Lys Asn Lys Thr Ser Glu Asp Ala Ala Ala Asp Tyr Val
                245                 250                 255

Gln Gly Val His Thr Leu Ser Gln Tyr Ala Asp Tyr Leu Val Ile Asn
```

```
                    260                 265                 270
Ile Ser Ser Pro Asn Thr Pro Gly Leu Arg Gln Leu Gln Gly Arg Lys
            275                 280                 285
Gln Leu Lys Asp Leu Val Lys Lys Val Gln Ala Ala Arg Asp Glu Met
        290                 295                 300
Gln Trp Gly Glu Gly Pro Pro Leu Leu Val Lys Ile Ala Pro
305                 310                 315                 320
Asp Leu Ser Lys Gln Asp Leu Glu Asp Ile Ala Val Ala Val Ala
                325                 330                 335
Leu Arg Val Asp Gly Leu Ile Ile Ser Asn Thr Thr Val Gln Arg Pro
            340                 345                 350
Asp Ser Ile Ser Gln Asn Pro Val Ala Gln Glu Ala Gly Leu Ser
            355                 360                 365
Gly Lys Pro Leu Phe Asp Met Ser Thr Asn Ile Leu Lys Glu Met Tyr
        370                 375                 380
Val Leu Thr Lys Gly Arg Ile Pro Leu Ile Thr Gly Gly Ile Ser
385                 390                 395                 400
Ser Gly Glu Asp Ala Tyr Lys Lys Ile Arg Ala Gly Ala Thr Leu Val
                405                 410                 415
Gln Leu Tyr Thr Ala Phe Ala Tyr Gly Gly Pro Ala Leu Ile Pro Asp
            420                 425                 430
Ile Lys Asp Glu Leu Ala Arg Cys Leu Glu Lys Asp Gly Tyr Lys Ser
            435                 440                 445
Ile Ser Glu Ala Val Gly Ala Asp Cys Arg
        450                 455

<210> SEQ ID NO 5
<211> LENGTH: 15
<212> TYPE: PRT
<213> ORGANISM: Artificial Sequence
<220> FEATURE:
<223> OTHER INFORMATION: by peptide synthesis

<400> SEQUENCE: 5

Leu Gly Thr Asp Ser Ala Pro His Asp Arg Arg Arg Lys Glu Cys
1               5                   10                  15

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6 aag gat ccg caa aaa tgg agc tct ca                              26

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7 aag gat cct cag aga gga gcc ggc aac                             27

<210> SEQ ID NO 8
<211> LENGTH: 24
<212> TYPE: DNA
```

```
-continued

<213> ORGANISM: Artificial Sequence
<220> FEATURE:
<223> OTHER INFORMATION: primer

<400> SEQUENCE: 8 aag gat cca tgg ccg gaa ggg ctg                                          24

<210> SEQ ID NO 9
<211> LENGTH: 44
<212> TYPE: DNA
<213> ORGANISM: Artificial Sequence
<220> FEATURE:
<223> OTHER INFORMATION: primer

<400> SEQUENCE: 9 aag gat cct tag tgg tgg tgg tgg tgg tgt ttg tgg gat ggg gc               44
```

DIHYDROOROTASE EXTRACTED FROM PLANTS

The present invention relates to the identification of plant dihydroorotase as a novel target for herbicidal active ingredients. The present invention furthermore relates to DNA sequences encoding a polypeptide with dihydroorotase (EC 3.5.2.3) activity. Also, the invention relates to the use of a nucleic acid encoding a protein with dihydroorotase activity of vegetable origin for the generation of a test system for identifying herbicidally active dihydroorotase inhibitors, and to inhibitors of plant dihydroorotase identified using these methods or this assay system. In addition, the present invention relates to a DNA sequence encoding a polypeptide with dihydroorotate dehydrogenase activity and to its use as auxiliary enzyme in a molecular assay system. Furthermore, the invention relates to the use of the nucleic acid encoding plant dihydroorotase for the generation of plants with an increased resistance to dihydroorotase inhibitors. In addition, the invention relates to a method of eliminating undesired vegetation, which comprises treating the plants to be eliminated with a compound which specifically binds to, and inhibits the function of, dihydroorotase encoded by a DNA sequence SEQ-ID No. 1 or by a DNA sequence hybridizing with this DNA sequence.

Plants are capable of synthesizing their cell components from carbon dioxide, water and inorganic salts.

This process is only possible by exploiting biochemical reactions for the synthesis of organic substances. Nucleotides, being constituents of the nucleic acids, must be synthesized de novo by the plants.

Not only the enzyme reactions of the de novo purine biosynthesis, but also the enzyme reactions of the de novo pyrimidine biosynthesis, are important for regulating the nucleotide metabolism. One of these enzymes is dihydroorotase. The enzyme catalyzes the elimination of water from carbamoyl aspartate and the cyclization to give dihydroorotate. The subsequent enzyme dihydroorotate dehydrogenase converts dihydroorotate into orotate via a redox reaction, see FIG. 1.

Genes which encode dihydroorotases were isolated from a variety of organisms. Complete cDNA sequences are known from bacteria (GenBank Acc. No. M97254, *Pseudomonas putida*, X84262 *Lactobacillus leichmannii*, AE000207 *Escherichia coli*, M97253 *Pseudomonas putida*, P74438 *Synechocystis*). In eukaryotes, dihydroorotase is a component of a multifunctional enzyme complex which is localized on an coding sequence (for example X03881 *Drosophila melanogaster*). In yeast, too, dihydroorotase is present in a multi-enzyme complex (Souciet et al., Mol. Gen. Genet. 207 (2-3), 314-319 (1987)). In plants, dihydroorotase is not a component of a polyfunctional polypeptide, but, similarly to what is the case in *E. coli*, exists as a separate enzyme. A plant dihydroorotase has hitherto only been isolated from *Arabidopsis thaliana* (Genbank Acc. No. AF000146; Zhou et al., Plant Physiol. 114 (1997), 1569).

The demonstration that an enzyme is suitable as herbicide target can be shown, for example, by reducing the enzyme activity by means of the antisense technology in transgenic plants. If this results in reduced growth, it can be concluded that the enzyme, whose activity is reduced, is suitable as site of action for herbicidal active ingredients. This was shown by way of example for acetolactate synthase in transgenic potato plants (Höfgen et al., Plant Physiology 107 (1995), 469-477).

It is an object of the present invention to prove that dihydroorotase in plants is a suitable herbicidal [sic] target, to isolate a complete plant cDNA encoding the enzyme dihydroorotase and its functional expression in bacterial or eukaryotic cells, and to generate an efficient and simple test system for carrying out inhibitor-enzyme binding studies.

We have found that this object is achieved by isolating a gene encoding the plant enzyme dihydroorotase, generating dihydroorotase antisense constructs, and functionally expressing dihydroorotase in bacterial or eukaryotic cells.

The present invention firstly relates to a DNA sequence SEQ-ID NO:1 comprising the coding region of a plant dihydroorotase from *Solanum tuberosum* (potato), see Examples 1 and 2.

The present invention furthermore relates to DNA sequences which are derived from this SEQ-ID NO:1 or hybridize herewith and which encode a protein which has the biological activity of a dihydroorotase.

Plants of the ROSa lines, which carry a dihydroorotase antisense construct, have been characterized in greater detail. The plants exhibit different degrees of growth retardation. The plant line ROSa-40 is affected to such an extent that no tubers are formed. Plants of this line are not viable in the greenhouse and must be maintained in vitro. A correlation between growth retardation and reduction in the dihydroorotase protein quantity can be found. This clear connection identifies dihydroorotase unambiguously as novel target protein for herbicidal active ingredients, see Examples 3-7.

To allow effective inhibitors of plant dihydroorotase to be found, suitable test systems must be provided with which inhibitor-enzyme binding studies can be carried out. To this end, for example, the complete cDNA sequence of *Solanum tuberosum* dihydroorotase is cloned into an expression vector (pQE, Qiagen) and overexpressed in *E. coli*, see Example 8.

Alternatively, however, the expression cassette comprising a DNA sequence SEQ-ID No. 1 can be expressed, for example, in other bacteria, in yeasts, fungi, algae, plant cells, insect cells or mammalian cells.

The dihydroorotase protein expressed with the aid of the expression cassette according to the invention is particularly suitable for finding dihydroorotase-specific inhibitors.

To this end, the dihydroorotase can be employed, for example, in an enzyme test in which the dihydroorotase activity in the presence and absence of the active ingredient to be tested is determined. By comparing the two activity determinations, a qualitative and quantitative statement can be made on the inhibitory behavior of the active ingredient to be tested.

The enzymatic detection developed hitherto for measuring the dihydroorotase activity by the method of Mazus and Buchowicz (Acta Biochimica Polonica (1968), 15 (4), 317-325) is based on detecting the orotate formed in a dihydroorotate-dehydrogenase-coupled reaction mixture at 280 nm. This assay is not suitable for mass screening. The method was therefore designed in such a way that NADH formed can be detected at 340 nm. To do this, a high activity of the auxiliary enzyme, the dihydroorotate dehydrogenase, is required. A commercially available preparation from Zymobacterium oroticum (Sigma) proved to be too impure for the NADH formation to be monitored. In order to be able to carry out mass screening, the specific dihydroorotate dehydrogenase activity must be at least ten times higher than that in the commercial preparation. Such an activity was obtained by isolating a plant dihydroorotate dehydrogenase and expressing it in yeast (*Saccharomyces cerevisiae*). This is why a test system was developed which was based on coupling plant dihydroorotase and plant dihydroorotate dehydrogenase. To this end, for example the gene encoding an *Arabidopsis thaliana* dihydroorotate/dehydrogenase was isolated (see Genbank Acc. No. x62909, Minet et al., Plant J. (1992), 2 (3), 417-422; Examples 9-11.

The test system according to the invention allows a large number of chemical compounds to be tested simply and rapidly for herbicidal properties. The method allows reproducibly to select in a directed fashion, from a multitude of substances, those with high potency in order to use these substances for subsequently carrying out other in-depth tests with which the skilled worker is familiar.

The invention furthermore relates to a method of identifying herbicidally active substances which inhibit the dihydroorotase activity in plants, consisting of the following steps
a) the generation of transgenic plants, plant tissues or plant cells which comprise an additional DNA sequence encoding an enzyme with dihydroorotase activity and which are capable of overexpressing an enzymatically active dihydroorotase;
b) applying a substance to transgenic plants, plant cells, plant tissues or plant parts and to untransformed plants, plant cells, plant tissues or plant parts;
c) determining the growth or the viability of the transgenic and the untransformed plants, plant cells, plant tissues or plant parts after application of the chemical substance; and
d) comparing the growth or the viability of the transgenic and the untransformed plants, plant cells, plant tissues or plant parts after application of the chemical substance;

where suppression of the growth or the viability of the untransformed plants, plant cells, plant tissues or plant parts without greatly suppressing the growth or the viability of the transgenic plants, plant cells, plant tissues or plant parts confirms that the substance of b) shows herbicidal activity and inhibits the dihydroorotase enzyme activity in plants.

The invention furthermore relates to a method of eliminating undesired vegetation, which comprises treating the plants to be eliminated with a compound which specifically binds to, and inhibits the function of, dihydroorotase encoded by a DNA sequence SEQ-ID No. 1 or a DNA sequence hybridizing with this DNA sequence.

The present invention furthermore relates to herbicidally active compounds which can be identified with the above-described test system.

Herbicidally active dihydroorotase inhibitors can be employed as defoliants, desiccants, haulm killers and, in particular, as weed killers. Weeds are to be understood as meaning, in the broadest sense, all plants which grow in locations where they are undesired. Whether the active ingredients found with the aid of the test system according to the invention act as total or selective herbicides depends, inter alia, on the quantity applied.

For example, herbicidally active dihydroorotase inhibitors can be used against the following weeds:

Dicotyledonous weeds of the genera:

*Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds of the genera:

*Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

The present invention also relates to expression cassettes whose sequences encode a *Solanum tuberosum* dihydroorotase or its functional equivalent. The nucleic acid sequence can be, for example, a DNA or a cDNA sequence.

In addition, the expression cassettes according to the invention comprise regulatory nucleic acid sequences which govern the expression of the coding sequence in the host cell. In accordance with a preferred embodiment, an expression cassette according to the invention comprises upstream, i.e. at the 5'-end of the coding sequence, a promoter and downstream, i.e. at the 3'-end, a polyadenylation signal and, if appropriate, other regulatory elements which are operably linked with the coding sequence, for the dihydroorotase gene, which is located in between. Operable linkage is to be understood as meaning the sequential arrangement of promoter, coding sequence, terminator and, if appropriate, other regulatory elements in such a way that each of the regulatory elements can fulfill its intended function when the coding sequence is expressed.

An expression cassette according to the invention is generated by fusing a suitable promoter with a suitable dihydroorotase DNA sequence and a polyadenylation signal using customary recombination and cloning techniques as they are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

The sequence homology between *Solanum tuberosum* dihydroorotase and *Arabidopsis thaliana* dihydroorotase is 78% identity at protein level. The homology was obtained using the program BLASTP (Altschul et al., Nucleic Acids Res. (1997) 25, 3389-3402), see Example 2.

The present invention also relates to functionally equivalent DNA sequences which encode a dihydroorotase gene and which, based on the total length of the gene, show 40 to 100% sequence homology with the DNA sequence SEQ-ID NO: 1.

Preferred subject matter of the invention are functionally equivalent DNA sequences which encode a dihydroorotase gene and which, based on the total length of the gene, show 60 to 100% sequence homology with the DNA sequence SEQ-ID NO: 1.

Particularly preferred subject matter of the invention are functionally equivalent DNA sequences which encode a dihydroorotase gene and which, based on the total length of the gene, show 80 to 100% sequence homology with the DNA sequence SEQ-ID NO: 1.

Functionally equivalent sequences which encode a dihydroorotase gene are, in accordance with the invention, those sequences which still have the desired functions, despite a differing nucleotide sequence. Functional equivalents thus encompass naturally occurring variants of the sequences described herein, and also artificial, for example chemically synthesized, artificial [sic] nucleotide sequences adapted to suit the codon usage of a plant. A functional equivalent is also to be understood as meaning, in particular, natural or artificial mutations of an originally isolated, dihydroorotase-coding sequence which continues to show the desired function. Mutations encompass substitutions, additions, deletions, exchanges or insertions of one or more nucleotide residues. Thus, for example, the present invention also encompasses those nucleotide sequences which are obtained by modifying this nucleotide sequence. The aim of such a modification can be, for example, to further delimit the coding sequence contained therein, or else, for example, insert more restriction enzyme cleavage sites.

Functional equivalents are also those variants whose function is weaker or stronger in comparison with the original gene or gene fragment.

In addition, the expression cassette according to the invention can also be employed for the transformation of bacteria, cyanobacteria, yeasts, filamentous fungi and algae with the purpose of producing sufficient amounts of the enzyme dihydroorotase.

The present invention furthermore relates to a *Solanum tuberosum* protein which comprises the amino acid sequence SEQ-ID NO:2 or derivatives or parts of this protein with dihydroorotase activity. In comparison with the *Arabidopsis thaliana* dihydroorotase, the homology at amino acid level is 78% identity.

The present invention also relates to plant proteins with dihydroorotase activity with an amino acid sequence homology to the *Solanum tuberosum* dihydroorotase of 20-100% identity.

Preferred plant proteins with dihydroorotase activity are those with an amino acid sequence homology to the *Solanum tuberosum* dihydroorotase of 50-100% identity.

Particularly preferred plant proteins with dihydroorotase activity are those with an amino acid sequence homology to the *Solanum tuberosum* dihydroorotase of 80-100% identity.

It is another object of the present invention to overexpress the dihydroorotase gene in plants in order to generate plants which tolerate dihydroorotase inhibitors.

Overexpressing the dihydroorotase-encoding gene sequence SEQ-ID NO: 1 in a plant results in an increased resistance to dihydroorotase inhibitors. The present invention also relates to the transgenic plants generated thus.

The expression efficacy of the transgenically expressed dihydroorotase gene can be determined, for example, in vitro by shoot meristem multiplication, or by a germination test. Also, an altered expression type and expression level of the dihydroorotase gene and their effect on the resistance to dihydroorotase inhibitors may be tested on test plants in greenhouse experiments.

The present invention furthermore relates to transgenic plants transformed with an expression cassette according to the invention comprising the DNA SEQ-ID No. 1, which plants have been made tolerant to dihydroorotase inhibitors by additional expression of the DNA sequence SEQ-ID No. 1, and to transgenic cells, tissues, parts and propagation material of such plants. Especially preferred are transgenic crop plants such as, for example, barley, wheat, rye, maize, soybeans, rice, cotton, sugar beet, canola, sunflowers, flax, hemp, potatoes, tobacco, tomatoes, oilseed rape, alfalfa, lettuce, and the various tree, nut and grapevine species, and also legumes.

The invention furthermore relates to plants, which, after expression of the DNA SEQ ID NO:1 in the plant, show an increased UMP content.

Increasing the uridine-5'-phosphate (UMP) content means, for the purposes of the present invention, the artificially acquired capability of an increased UMP biosynthesis performance by functionally overexpressing the dihydroorotase gene in the plant compared to the non-genetically-engineered plant for at least one plant generation.

Especially preferred sequences are those which ensure targeting into the apoplast, into plastids, into the vacuole, into the mitochondrium or into the endoplasmatic reticulum (ER) or which, due to a lack of suitable operative sequences, ensure that the product remains in the compartment of formation, the cytosol (Kermode, Crit. Rev. Plant Sci. 15, 4 (1996), 285-423).

For example, the plant expression cassette can be incorporated into the tobacco transformation vector pBinAR (see Example 3).

A suitable promoter of the expression cassette according to the invention is, in principle, any promoter which is capable of governing the expression of foreign genes in plants. In particular, a plant promoter or a promoter derived from a plant virus is preferably used. Especially preferred is the cauliflower mosaic virus CaMV 35S promotor (Franck et al., Cell 21(1980), 285-294). This promoter contains various recognition sequences for transcriptional effectors which in their totality lead to permanent and constitutive expression of the introduced gene (Benfey et al., EMBO J. 8 (1989), 2195-2202).

The expression cassette according to the invention may also comprise a chemically inducible promoter which allows expression of the exogenous dihydroorotase gene in the plant to be governed at a particular point in time. Such promoters, for example the PRP1 promotor (Ward et al., Plant. Mol. Biol. (1993) 22, 361-366), a salicylic-acid-inducible promoter (WO 95/1919443), a benzenesulfona-mide-inducible promoter (EP 388186), a tetracyclin-inducible promoter (Gatz et al., Plant J. (1992) 2, 397-404), an abscisic-acid-inducible promoter (EP0335528) or an ethanol- or cyclohexanone-inducible promoter (WO 93/21334) are described in the literature and can be used, inter alia.

Furthermore, especially preferred promoters are those which ensure expression in tissues or parts of the plant in which the biosynthesis of purins or their precursors takes place. Promoters which ensure leaf-specific expression may be mentioned in particular. Promoters which may be mentioned are the potato cytosolic FBPase or the potato ST-LSI promoter (Stockhaus et al., EMBO J., (1989) 8, 2445-251 [sic]).

A foreign protein can be expressed stably in the seeds of transgenic tobacco plants to an extent of 0.67% of the total soluble seed protein with the aid of a seed-specific promoter (Fiedler and Conrad, Bio/Technology (1995) 10, 1090-1094). The expression cassette according to the invention can therefore comprise, for example, a seed-specific promoter (preferably the phaseolin promotor, the USP or LEB4 promotor), the LEB4 signal peptide, the gene to be expressed, and an ER retention signal.

The inserted nucleotide sequence encoding a dihydroorotase can be generated synthetically or obtained naturally or comprise a mixture of synthetic and natural DNA components. In general, synthetic nucleotide sequences are generated which have codons which are preferred by plants. These codons which are preferred by plants can be determined by codons with the highest protein frequency which are expressed in most of the plant species of interest. When preparing an expression cassette, it is possible to manipulate various DNA fragments so as to obtain a nucleotide sequence which expediently reads in the correct direction and which is equipped with a correct reading frame. To link the DNA fragments to each other, adapters or linkers may be attached to the fragments.

Other suitable DNA sequences are artificial DNA sequences as long as they mediate, as described above by way of example, the desired property of increasing the UMP content in the plant by overexpressing the dihydroorotase gene in crop plants. Such artificial DNA sequences can be determined, for example, by backtranslating proteins which have been constructed by means of molecular modeling and which exhibit dihydroorotase activity, or by in vitro selection. Especially suitable are encoding DNA sequences which have been obtained by backtranslating a polypeptide sequence in accordance with the host-plant-specific codon usage. The specific codon usage can be determined readily by a skilled worker familiar with plant-genetic-engineering methods by means of computer evaluations of other, known genes of the plant to be transformed.

Further suitable equivalent nucleic acid sequences according to invention which may be mentioned are sequences which encode fused proteins, component of the fused protein being a plant dihydroorotase polypeptide or a functionally equivalent portion thereof. The second portion of the fused protein can be, for example, a further enzymatically active polypeptide or an antigenic polypeptide sequence with the aid of which detection for dihydroorotase expression is possible (for example myc-tag or his-tag). However, it is preferably a regulatory protein sequence such as, for example, a signal or transit peptide, which leads the dihydroorotase protein to the desired site of action.

Expediently, the promoter regions according to the invention and the terminator regions should be provided, in the direction of transcription, with a linker or polylinker comprising one or more restriction sites for insertion of this sequence. As a rule, the linker has 1 to 10, in most cases 1 to 8, preferably 2 to 6, restriction sites. In general, the linker within the regulatory regions has a size less than 100 bp, frequently less than 60 bp, but at least 5 bp. The promoter according to the invention can be native, or homologous, or else foreign, or heterologous, to the host plant. The expression cassette according to the invention comprises, in the 5'-3'-direction of transcription, the promoter according to the invention, any sequence and a region for transcriptional termination. Various termination regions may be exchanged for each other as desired.

Manipulations which provide suitable restriction cleavage sites or which eliminate the excess DNA or excess restriction cleavage sites may also be employed. In vitro mutagenesis, prime repair, restriction or ligation may be used in cases where insertions, deletions or substitutions such as, for example, transitions and transversions, are suitable. Complementary ends of the fragments may be provided for ligation in the case of suitable manipulations such as, for example, restriction, chewing back or filling in overhangs for blunt ends.

Preferred polyadenylation signals are plant polyadenylation signals, preferably those which correspond essentially to *Agrobacterium tumefaciens* T-DNA polyadenylation signals, in particular those of gene 3 of the T-DNA (octopine synthase) of the Ti-plasmid pTiACH5 (Gielen et al., EMBO J. 3 (1984) 835 ff), or functional equivalents.

For transforming a host plant with a dihydroorotase-encoding DNA, an expression cassette according to the invention is incorporated, as insertion, into a recombinant vector whose vector DNA comprises additional functional regulatory signals, for example sequences for replication or integration. Suitable vectors are described, inter alia, in "Methods in Plant Molecular Biology and Biotechnology" (CRC Press), Chapter 6/7, pp. 71-119.

The transfer of foreign genes into the genome of a plant is termed transformation. It exploits the above-described methods for transforming and regenerating plants from plant tissues or plant cells for transient or stable transformation. Suitable methods are protoplast transformation by polyethylene glycol-induced DNA uptake, the biolistic method using the gene gun, electroporation, incubation of dry embryos in DNA-containing solution, microinjection and *agrobacterium*-mediated gene transfer. The abovementioned methods are described in, for example, B. Jenes et al., Techniques for Gene Transfer, in: Transgenic Plants, Vol. 1, Engineering and Utilization, edited by S. D. Kung and R. Wu, Academic Press (1993) 128-143 and in Potrykus Annu. Rev. Plant Physiol. Plant Molec. Biol. 42 (1991) 205-225). The construct to be expressed is preferably cloned into a vector which is suitable for the transformation of *Agrobacterium tumefaciens*, for example pBin19 (Bevan et al., Nucl. Acids Res. 12 (1984) 8711).

*Agrobacteria* transformed with an expression cassette according to the invention can equally be used in a known manner for transforming plants, in particular crop plants such as cereals, maize, soybeans, rice, cotton, sugar beet, canola, sunflowers, flax, hemp, potatoes, tobacco, tomatoes, oilseed rape, alfalfa, lettuce and the various tree, nut and grapevine species, and legumes, for example by bathing wounded leaves or leaf sections in an agrobacterial suspension and subsequently growing them in suitable media.

The biosynthesis site of pyrimidines is, generally, the leaf tissue, so that leaf-specific expression of the dihydroorotase gene is useful. However, it is obvious that the pyrimidine biosynthesis need not be limited to the leaf tissue, but may also take place in all other remaining parts of the plant in a tissue-specific fashion, for example in fatty seeds.

Moreover, constitutive expression of the exogenous dihydroorotase gene is advantageous. On the other hand, inducible expression may also be desirable.

Using the above-cited recombination and cloning techniques, the expression cassettes according to the invention can be cloned into suitable vectors which allow them to be multiplied, for example in *E. coli*. Suitable cloning vectors are, inter alia, pBR332, pUC series, M13 mp series and pACYC184. Especially suitable are binary vectors, which are capable of replication both in *E. coli* and in *agrobacteria*.

The present invention furthermore relates to the use of an expression cassette according to the invention for the transformation of plants, plant cells, plant tissues or parts of plants. The preferred aim of the invention is to increase the dihydroorotase content in the plant.

Depending on the choice of the promoter, expression may take place specifically in the leaves, in the seeds or other parts of the plant. Such transgenic plants, their propagation material and their plant cells, tissue or parts are a further subject of the present invention.

BRIEF DESCRIPTION OF THE DRAWINGS

Exemplary methods and arrangements conducted and configured according to the advantageous solutions presented herein are depicted in the accompanying drawings wherein:

FIG. 2 is an illustration of dihydroorotase protein quantity in leaf and tuber of selected transformants of line ROSa; and, FIG. 3 is an illustration of Dihydroorotase mRNA content in fully grown leaves of selected transformants of line ROSa.

Figure 1:
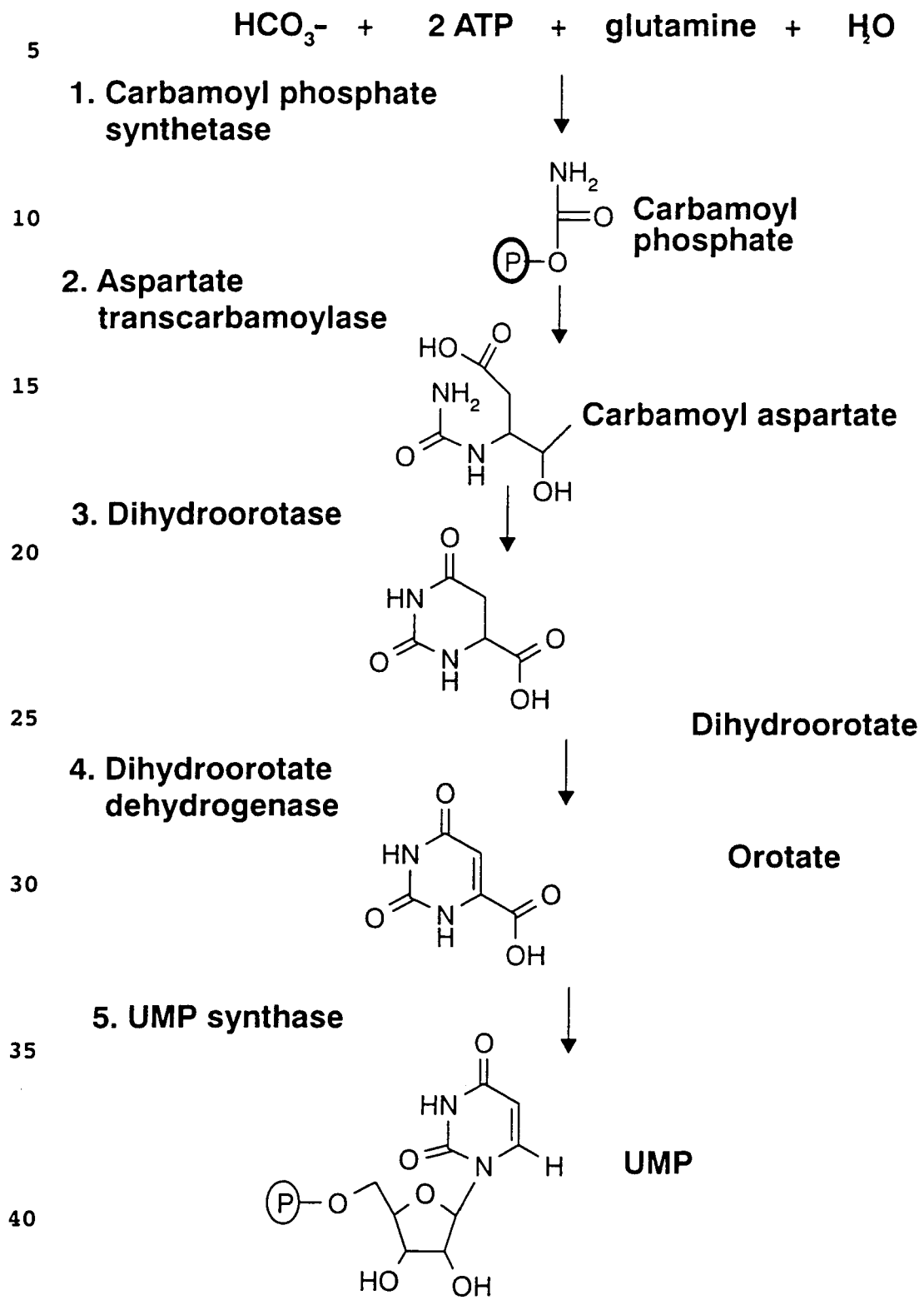
FIG. 1 is a flow diagram illustrating the enzymatic conversion of dihydroorotate into orotate via a redox reaction by dihydroorotate dehydrogenase.

The invention is illustrated by the examples which follow, but not limited thereto:

EXAMPLES

Genetic engineering methods on which the use examples are based:

General Cloning Methods

Cloning methods such as, for example, restriction cleavage, agarose gel electrophoresis, purification of DNA fragments, transfer of nucleic acids to nitrocellulose and nylon membranes, linking DNA fragments, transformation of *Escherichia coli* cells, growing bacteria, and the sequence analysis of recombinant DNA, were carried out as described by Sambrook et al. (1989) (Cold Spring Harbor Laboratory Press: ISBN 0-87969-309-6).

Sequence Analysis of Recombinant DNA

Recombinant DNA molecules were sequenced using an ABI laser fluorescence DNA sequencer following the method of Sanger (Sanger et al. (1977), Proc. Natl. Acad. Sci. USA 74, 5463-5467). Fragments resulting from a polymerase chain reaction were sequenced and checked in order to avoid polymerase errors in constructs to be expressed.

Example 1

Isolation of a cDNA Encoding a Functional Plant Dihydroorotase

A clone encoding dihydroorotase was obtained from potatoes by functional complementation of an *E. coli* mutant. The mutant used was the mutant CGSC5152 (CS101-2U5) of the *E. coli* Genetic Stock Center, which carries a mutation in the pyrC gene locus encoding a dihydroorotase. Complementation was effected by electrotransformation of competent cells of strain CGSC5152 with a cDNA library in the vector plasmid pBS SK–. The underlying lambda ZAPII library (Stratagene) was cloned in an undirected fashion with EcoRI/NotI linkers following standard procedures. The RNA template for the cDNA was isolated from sink leaves (small 1-cm-leaflets harvested from 10-week-old potato plants, grown in the greenhouse).

The transformed *E. coli* cells were plated on M9 minimal medium (Sambrook et al., 1989) complemented with methionine (20 mg/l), ampicillin (100 mg/l) and IPTG (2.5 mM). In total, 4 micrograms of the library were transformed in 8 batches, giving rise to 36 clones which, following examination by means of restriction cleavage, proved to be identical.

Example 2

Sequence Analysis of the cDNA Clones Encoding a Protein with Dihydroorotase Activity The resulting 36 cDNA clones encode a polypeptide with homology to dihydroorotases from other organisms. The homology was obtained using the program BLASTP (Altschul et al., Nucleic Acids Res. (1997) 25, 3389-3402). Accordingly, the protein has 78% identity with *Arabidopsis thaliana* dihydroorotase, 58% identity with *Synechocystis dihydroorotase*, 55% identity with *E. coli* and *Pseudomonas putida* dihydroorotase. The longest clone was termed pyrCSt5. The plasmid was given the name pBSSK-pyrCSt5.

The cDNA (see SEQ-ID No. 1) has an open reading frame of 1046 base pairs with a stop sodon in position 1047-1049. The amino acid sequence starts with the third base in the reading frame and can be translated into a polypeptide 348 amino acids in length (see SEQ-ID No. 2). This corresponds to the length of prokaryotic dihydroorotase-coding sequences.

Owing to the reading frame of the present cDNA sequence, it cannot be deduced with certainty whether it might possibly be a form localized in the plastids or a cytosolic form.

Example 3

Generation of Plant Expression Cassettes

A 35S CaMV promoter was inserted into plasmid pBin19 (Bevan et al., Nucl. Acids Res. 12 (1980), 8711) in the form of an EcoRI-KpnI fragment (corresponding to nucleotides 6909-7437 of the cauliflower mosaic virus (Franck et al., Cell 21 (1980), 285). The polyadenylation signal of gene 3 of the T-DNA from Ti-plasmid pTiACH5 (Gielen et al., EMBO J. 3 (1984), 835), nucleotides 11749-11939 was isolated as a PvuII-HindIII fragment and, after addition of SphI linkers, cloned into the PvuII cleavage site between the SphI-HindIII cleavage site of the vector. This gave rise to plasmid pBinAR(Höfgen and Willmitzer, Plant Science 66 (1990), 221-230). Cloning of a construct of pyrCSt5 in antisense orientation in pBinAR was done by an Asp718 cleavage site (internal cleavage site of 964 bp) and a BamHI cleavage site (from the polylinker).

Example 4

Generation of Transgenic Potato Plants

Potato plants (cv. Solara) were transformed with the aid of *Agrobacterium tumefaciens* using the corresponding construct pBinAR-anti-pyrCSt5. The plasmid was transformed into *Agrobacterium tumefaciens* C58Cl:pGV2260 (Deblaere et al., Nucl. Acids. Res. 13 (1984), 4777-4788). To transform potatoes by the method of Rocha-Sosa et al. (EMBO J., 8 (1988), 23-29), a 1:50 dilution of an overnight culture of a positively transformed agrobacterial colony in Murashige-Skoog medium (Physiol. Plant., (1962), 473) was used. Leaf disks of sterile plants (in each case approx. 1 cm²) were incubated for 5-10 minutes in a 1:50 agrobacterial solution in a petri dish. This was followed by incubation in the dark for 2 days at 20° C. on MS medium. Cultivation was subsequently continued in a 16 hour light/8 hour dark photoperiod. For shoot induction, explants were transferred weekly to MS medium supplemented with 500 mg/l claforan (cefotaxime-sodium), 50 mg/l kanamycin and plant hormones (Rocha-Sosa et al., EMBO J., 8, 23-29, 1989) and 1.6 g/l glucose. Growing shoots were transferred to MS medium supplemented with 2% sucrose, 250 mg/l claforan and 0.8% Bacto-agar.

Regenerated shoots are obtained on 2MS medium supplemented with kanamycin and claforan, transferred into the soil after they have struck roots and, after culture for two weeks in a controlled-environment cabinet in a 16-hour-light/8-hour-dark photoperiod at an atmospheric humidity of 50%, examined for expression of the foreign gene, altered metabolite contents and phenotypic growth characteristics. Altered nucleotide contents may be determined, for example, by the method of Stitt et al. (FEBS Letters, 145 (1982), 217-222).

Example 5

Analysis of Total RNA from Plant Tissues

Total RNA from plant tissues was isolated as described by Logemann et al., Anal. Biochem. 163 (1987), 21. For the analysis, in each case 20 micrograms of RNA were separated in a formaldehyde-containing 1.5% strength agarose gel and transferred to Duralon UV membranes (Stratagene).

To detect specific transcripts, digoxygenine-labeled probes were prepared by means of PCR following the manufacturer's instructions and used for hybridization (DIG EasyHyb, Boehringer). Then, the membranes were washed for 3×20 minutes in wash buffer (2×SSC, 0.1% SDS) at 60° C. Detection was carried out by luminescence and exposure to Hyperfilm ECL (Amersham) using the Boehringer DIG detection system with CDP-Star as substrate.

Resulting individual transgenic plants of lines ROSa-34, -31, -10, -19, -9 and -3 are shown in FIG. 3 as test plants at RNA level. A band is recognizable at 1.6 kb in accordance with the expected dihydroorotase transcript size and, in the case of plants ROSa-3, -9, -31, -34, the 1.1 kb antisense transcript. A marked reduction in RNA quantity can be found, in particular, in the case of plant ROSa-9.

Example 6

Detection of the Potato Dihydroorotase Protein in Tuber and Leaf Tissues.

To generate a polyclonal serum against the dihydroorotase polypeptide, a peptide sequence from the potato dihydroorotase amino acid sequence was chosen. The peptide LGTDSAPHDRRRKEC (SEQ ID NO:5) was synthesized by a commercial company (Eurogentec, Seraing, Belgium) and coupled to KLH (keyhole limpet protein) via the C-terminal cysteine. The conjugate was employed, again, by the commercial company (Eurogentec) for immunizing rabbits and antisera against the peptide were obtained. In Western blot experiments, the antiserum specifically recognizes the potato polypeptide. To this end, protein was subjected to an SDS polyacrylamide gel electrophoresis under denaturing conditions, transferred to nitrocellulose membranes and detected by means of immunodetection following the manufacturer's instructions (ECL-System, Amersham). Transgenic plants of the ROSa lines were characterized with the aid of the antiserum. Lines -3, -9 and -40 show different degrees of protein reduction in the leaf, see FIG. 2. Plant -40 does not form tubers. Plants -3 and -9 also show a correspondingly greatly reduced dihydroorotase protein quantity in tubers.

Example 7

Phenotypic Analysis of Transgenic Plants.

Plants of lines ROSa, which carry a dihydroorotase antisense construct were characterized in greater detail. The plants show differing degrees of growth retardation. Plant line ROSa-40 is affected to such an extent that no tubers are formed. Plants of this line are not viable in the greenhouse and must be maintained in vitro. A correlation can be found between growth retardation and reduction in dihydroorotase protein quantity. This clear connection identifies potato dihydroorotase unambiguously as novel target protein for herbicidal active ingredients.

Example 8

Generation of Overexpression Vectors in E. Coli

The following oligonucleotide sequences were derived from the sequence determined, and provided with a BamHI restriction cleavage site and with two base overhangs.

1. 5'-primer aaggatccGCAAAAATGGAGCTCTCA (SEQ ID NO:6)

2. 3'-primer aaggatccTCAGAGAGGAGCCGGCAAC (SEQ ID NO:7)

The PCR reaction mixtures contained 8 ng/μl pBSSK-pyrCSt5 DNA, 0.5 μM of the corresponding oligonucleotides, 200 μM nucleotides (Pharmacia), 50 mM KCl, 10 mM Tris-HCl (pH 8.3 at 25° C.), 1.5 mM MgCl$_2$ and 0.02 U/μl Taq polymerase (Perkin Elmer). The amplification conditions were set as follows:

| | |
|---|---|
| Denaturation temperature: | 92° C., 1 min |
| Annealing temperature: | 52° C., 1 min |
| Elongation temperature: | 72° C., 2.5 min |
| Number of cycles: | 30 |

The PCR fragments were cloned into the overexpression vector pQE9 via BamHI and employed for protein production by means of IPTG induction following standard methods (see Handbuch: The QiaExpressionist, Qiagen, Hilden).

Example 9

Test System for Measuring the Dihydroorotase Activity

The enzymatic detection developed to date for measuring the dihydroorotase activity by the method of Mazus and Buchowicz, (Acta Biochimica Polonica (1968), 15(4), 317-325) is based on detecting the orotate formed at 280 nm in a dihydroorotate-dehydrogenase-coupled reaction mixture. Prerequisite for doing so is a high activity of the auxiliary enzyme, viz. dihydroorotate dehydrogenase. A commercially available preparation from Zymobacterium oroticum (Sigma) proved to be too contaminated.

In order to be able to carry out a mass screening, the specific dihydroorotate dehydrogenase activity must be at least ten times higher than is the case in the commercial preparation. Such an activity was obtained by preparing a dihydroorotate dehydrogenase activity from Neurospora crassa (R. W. Miller, Methods in Enzymology LI, 1978, 63-69) after cloning a plant dihydroorotate dehydrogenase and its expression in yeast (Saccharomyces cerevisiae). A further improvement of the test system was achieved by carrying out the measurement at 340 nm.

First, an Arabidopsis thaliana dihydroorotate dehydrogenase was isolated (see Genbank Acc. No. X62909, Minet et al., Plant J. (1992), 2 (3), 417-422).

The following oligonucleotide sequences were derived from the database entry of the dihydroorotate dehydrogenase sequence:

1. 5'-primer aaggatccatggccggaagggctg (SEQ ID NO:8)

2. 3'-primer aaggatccttagtggtggtggtggtggtgtttgtgggatggggc (SEQ ID NO:9)

The PCR reaction mixtures contained 10 ng of plasmid DNA from an Arabidopsis thaliana cDNA in vector pFL61 (ATCC 77600), 0.5 microM [sic] of the corresponding oligonucleotides, 200 μM nucleotides (Pharmacia), 50 mM KCl, 10 mM Tris-HCl (pH 8.3 at 25° C.), 1.5 mM MgCl$_2$ and 0.02 U/µl Taq polymerase (Perkin Elmer). The amplification conditions were set as follows:

| | |
|---|---|
| Denaturation temperature: | 92° C., 0.5 min |
| Annealing temperature: | 60° C., 0.5 min |
| Elongation temperature: | 72° C., 1.5 min |
| Number of cycles: | 35 |

The resulting PCR fragment was first cloned into the yeast expression vector pYES2 (Invitrogen) via the BamHI cleavage sites. The construct generated was named pYES2-pyrDAt.

Example 10

Cloning of a Plant Dihydroorotate Dehydrogenase from Tobacco

Furthermore, the PCR fragment described in Example 9 was applied for a heterologous screening in a tobacco phage cDNA library. The cDNA employed for generating the tobacco phage cDNA library was obtained from RNA from tobacco cell suspension cultures. The cDNA library was generated following the manufacturer's instructions (Stratagene). 3.0×10$^5$ lambda phages of the Nicotiana tabacum cDNA library were plated on agar plates with E. coli XLI-Blue as bacterial strain.

The phage DNA was transferred to nylon filters (Duralon UV, Stratagene) by means of standard methods (Sambrook et al. (1989); Cold Spring Harbor Laboratory Press: ISBN 0=87969-309-6) and fixed on the filters. The hybridization probe used was the above-described PCR fragment, which was DIG-labeled with the aid of the labeling and detection system (Boehringer, Mannheim) following the manufacturer's instructions. Hybridization of the membrane was carried out for 16 hours at 42° C. in DIG EasyHyb (Boehringer). The filters were subsequently washed for 3×20 minutes in 2×SSC, 0.1% SDS at 60° C. Positively hybridizing phages were on Hyperfilm ECL (Amersham) by luminescence with the Boehringer DIG detection system using CDP-Star as substrate, and purified and isolated by standard techniques.

Ten identical clones resulted, of which clone pyrDT10 was sequenced completely (SEQ-ID No. 3). An EcoRI digest of the clone shows an EcoRI fragment 1962 base pairs in size with an open reading frame of 458 amino acids, a start codon in position 305-307 and a stop codon in position 1679-1681. The deduced amino acid sequence (SEQ-ID No. 4) of the tobacco dihydroorotate dehyrogenase exhibits 72% identity with the Arabidopsis amino acid sequence, 51% identity with the rat amino acid sequence, 43% identity with the yeast amino acid sequence, 37% identity with the E. coli amino acid sequence. The identity was obtained using the program BLASTP (Altschul et al., Nucleic Acids Res. (1997) 25, 3389-3402).

The following oligonucleotide sequences were derived from the sequence determined, and provided with a KpnI restriction cleavage site and two base overhangs.

1. 5'-primer ggggtaccatgagacaaagggttggatt 2. 3'-primer ggggtaccttagtggtggtggtggtg-gtggagaggagccggcaacca The PCR reaction mixtures contained 5 ng/µl pBSSK-pyrDT10 DNA, 0.5 µM of the corresponding oligonucleotides, 200 µM nucleotides (Pharmacia), 50 mM KCl, 10 mM Tris-HCl (pH 8.3 at 25° C.), 1.5 mM MgCl$_2$ and 0.02 U/µl Taq polymerase (Perkin Elmer). The amplification conditions were set as follows:

| | |
|---|---|
| Denaturation temperature: | 92° C., 1 min |
| Annealing temperature: | 52° C., 1 min |
| Elongation temperature: | 72° C., 2.5 min |
| Number of cycles: | 30 |

The PCR fragment of the tobacco dihydroorotate dehydrogenase was cloned into the yeast expression vector pYES2 (Invitrogen) via KpnI cleavage sites. This construct (pYES-pyrDT10) and the Arabidopsis dihydroorotate dehydrogenase construct pYES2-pyrDAt were inserted into the ural yeast mutant for complementation (Minet et al., Gene (1992), 121(2), 393-6). Resulting yeast clones were grown in liquid culture overnight in complete medium supplemented with 1% galactose.

Example 11

Enzyme Isolation of Plant Dihydroorotase and Dihydroorotate Dehydrogenase, and Measurement of the Dihydroorotase Activity The dihydroorotase E. coli expression cultures, and the yeast expression culture containing the tobacco (or Arabidopsis) dihydroorotate dehydrogenase, were in each case disrupted separately by means of pressure disruption methods using the French Press under maximum pressure in a 20 ml pressurized chamber, or with the aid of a glass ball mill (IMA Desintegrator). Per 1 g of cell pellet, 10 ml of buffer (0.1M KH$_2$PO$_4$; pH 7.5; 0.4M sucrose, 0.1 mM DTT) are used. By adding a 2.5-fold amount of glass beads (d=0.5 mm), the pellet is disrupted in the glass ball mill for 20 minutes at 4° C. and 2500 rpm. The batch is centrifuged for 20 minutes at 4° C. and 100,000 g. The enzyme activity was determined in a photometric assay by measurement in a photometer (Uvikon 933, Kontron) at 340 nm. The choice of the overexpression vectors also allowed the dihydroorotase and the dihydroorotate dehydrogenase to be purified via the histidin anchor by standard methods in one step under native conditions if the disruption buffer was free from DTT (cf. also Handbuch: The QiaExpressionist, Qiagen, Hilden). The eluates were subjected to dialysis to change the buffer to 20 mM potassium phosphate buffer pH 6.1; 5 mM MgCl$_2$; 1 mM DTT; 10 mM cysteine; 10 µM ZnCl$_2$, 20 µM NAD. In each case 10-100 µl of the resulting enzyme fraction was made up with buffer to 700 µl and measured against a reference cell containing 700 µl reaction buffer and 100 µl of a protein homogenate of untransformed E. coli culture. The reaction was started using 7 mM carbamyl aspartate. Identical quantities of total protein were employed for measuring the untransformed or transformed E. coli extracts. As an alternative to plant dihydroorotate dehydrogenase activities expressed in yeasts, it is possible to employ a dihydroorotate dehydrogenase activity prepared from Neurospora crassa, see R. W. Miller, Dihydroorotate dehydrogenase, (in: Methods in Enzymology 51 (1978), 63-69).

Alternatively, the dihydroorotase may also be measured in a less sensitive colorimetric assay by the method of Prescott and Jones (Anal. Biochem. (1969) 32, 408-419) without being coupled to dihydroorotate dehydrogenase. To this end, the dihydroorotase activity was measured in 50 mM Tris-HCl, 1 mM dihydroorotate (pH 8.5) after incubation at 37° C. by detecting the carbamoyl aspartate formed. Prerequisite to this is the protein preparation with high protein activity which has been described in this example.

The potato dihydroorotase activity measured in the assay systems described can be reduced with known dihydroorotase inhibitors such as 6-L-thiodihydroorotate or 2-oxo-1,2,3,6-tetrahydropyrimidine-4,6-dicarboxylate (Christopherson et al., Biochemical Society Transactions 23: 888-893, 1995).

---

We claim:

1. A method for screening herbicidally active substances which inhibit the activity of plant dihydroorotase, comprising:
generating, in a first step, dihydroorotase or a protein having the enzymatic activity of a dihydroorotase, and in a second step, measuring activity of the dihydroorotase in the presence and absence of a test substance, wherein the dihydroorotase or protein is generated from the expression of a DNA sequence having a homology of at least 80% with SEQ ID NO:1.

2. The method of claim 1, wherein the dihydroorotase or protein is generated from the expression of SEQ ID NO: 1.

3. The method of claim 1, wherein the dihydroorotase or protein is generated from the expression of a DNA sequence having a homology of at least 95% with SEQ ID NO: 1.

4. The method as claimed in claim 1, wherein the dihydroorotase or protein is measured in a high-throughput screening assay.

5. The method of claim 2, which comprises generating, in the first step, dihydroorotase using the DNA sequence of SEQ ID NO: 1.

6. The method of claim 1 further comprising:
selecting the test substance which has a herbicidal activity.

7. The method of claim 1 further comprising:
identifying a herbicidally active test substance which inhibits dihydroorotase.

8. The method of claim 1, wherein the activity is measured in a photometric assay.

9. The method of claim 8, wherein the photometric assay is measured in a photometer.

10. The method of claim 8, wherein the photometric assay is read at 340 nm.

11. The method of claim 1, wherein the activity is measured in a colorimetric assay.

12. The method of claim 11, wherein the activity is measured by detecting formation of carbamoyl aspartate.

13. An assay system based on a dihydroorotase or a protein having the enzymatic activity of a dihydroorotase, for identifying inhibitors of plant dihydroorotase, comprising:
incubating the dihydroorotase or protein with a test substance to be studied, said dihydroorotase or protein generated from the expression of a DNA sequence having a homology of at least 80% with SEQ ID NO:1, and after a suitable reaction time, determining the enzymatic activity of the protein in comparison with the activity of the protein in the absence of the test substance.

14. The assay system of claim 13, wherein the dihydroorotase or the protein is generated from of SEQ ID NO: 1.

15. The assay system of claim 14, wherein the dihydroorotase or the protein is generated from the expression of a DNA sequence having a homology of at least 95% with SEQ ID NO: 1.

16. A method for screening herbicidally active substances which inhibit the activity of plant dihydroorotase comprising:
generating a dihydroorotase or a protein having the enzymatic activity of a dihydroorotase, wherein said dihydroorotase or said protein are generated from the expression of a DNA sequence having a homology of at least 80% with SEQ ID NO: 1.
measuring an activity of the dihydroorotase in the presence and absence of a test substance; and
identifying a herbicidally active test substance which inhibits the dihydroorotase, wherein the activity is measured in one of a photometric and a calorimetric assay.

17. The assay system of claim 14, wherein the dihydroorotase or the protein is generated from the expression of a DNA sequence having a homology of at least 95% with SEQ ID NO:1.

* * * * *

UNITED STATES PATENT AND TRADEMARK OFFICE
CERTIFICATE OF CORRECTION

| | | |
|---|---|---|
| PATENT NO. | : 7,320,877 B1 | Page 1 of 1 |
| APPLICATION NO. | : 10/070277 | |
| DATED | : January 22, 2008 | |
| INVENTOR(S) | : Ehrhardt et al. | |

It is certified that error appears in the above-identified patent and that said Letters Patent is hereby corrected as shown below:

In Claim 14, column 28, line 34, please delete the phrase:

"from of"

and please substitute therefor:

--from--

Signed and Sealed this

Twenty-ninth Day of April, 2008

JON W. DUDAS
*Director of the United States Patent and Trademark Office*